US011607264B2

United States Patent
Heckel et al.

(10) Patent No.: US 11,607,264 B2
(45) Date of Patent: Mar. 21, 2023

(54) SYSTEMS AND METHODS FOR CALCULATING TISSUE IMPEDANCE IN ELECTROSURGERY

(71) Applicant: Covidien LP, Mansfield, MA (US)

(72) Inventors: Donald W. Heckel, Thornton, CO (US); Andrey Belous, Longmont, CO (US)

(73) Assignee: Covidien LP, Mansfield, MA (US)

( * ) Notice: Subject to any disclaimer, the term of this patent is extended or adjusted under 35 U.S.C. 154(b) by 592 days.

(21) Appl. No.: 16/696,193

(22) Filed: Nov. 26, 2019

(65) Prior Publication Data

US 2020/0093534 A1 Mar. 26, 2020

Related U.S. Application Data

(62) Division of application No. 14/562,907, filed on Dec. 8, 2014, now Pat. No. 10,492,850.

(Continued)

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1206* (2013.01); *A61B 18/1445* (2013.01); *G05B 15/02* (2013.01); *G06F 17/10* (2013.01); *A61B 2018/0063* (2013.01); *A61B 2018/00577* (2013.01); *A61B 2018/00589* (2013.01);
(Continued)

(58) Field of Classification Search
None
See application file for complete search history.

(56) References Cited

U.S. PATENT DOCUMENTS

| 4,186,437 A | 1/1980 | Cuk |
| 4,727,874 A | 3/1988 | Bowers et al. |

(Continued)

FOREIGN PATENT DOCUMENTS

| DE | 179607 C | 11/1906 |
| DE | 390937 C | 3/1924 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Ronald Hupczey, Jr.
(74) *Attorney, Agent, or Firm* — Carter, DeLuca & Farrell LLP

(57) ABSTRACT

An electrosurgical generator and associated methods determine a real part of the impedance of treated tissue. The electrosurgical generator includes an output stage, a plurality of sensors, and a controller that controls the output stage. The controller includes a signal processor that determines an RMS voltage, an RMS current, an average power, and a real part of the impedance of the treated tissue based on measured voltage and current by using a plurality of averaging filters. The controller controls the output stage to generate electrosurgical energy based on at least the determined real part of the impedance.

10 Claims, 10 Drawing Sheets

Related U.S. Application Data

(60) Provisional application No. 61/975,070, filed on Apr. 4, 2014.

(51) Int. Cl.
   *G05B 15/02* (2006.01)
   *G06F 17/10* (2006.01)
   *A61B 18/00* (2006.01)

(52) U.S. Cl.
   CPC ........... *A61B 2018/00601* (2013.01); *A61B 2018/00642* (2013.01); *A61B 2018/00648* (2013.01); *A61B 2018/00702* (2013.01); *A61B 2018/00755* (2013.01); *A61B 2018/00767* (2013.01); *A61B 2018/00779* (2013.01); *A61B 2018/00827* (2013.01); *A61B 2018/00875* (2013.01); *A61B 2018/00892* (2013.01)

(56) References Cited

U.S. PATENT DOCUMENTS

| | | | |
|---|---|---|---|
| 5,632,272 A | 5/1997 | Diab et al. | |
| 5,722,975 A * | 3/1998 | Edwards | A61B 18/1492 606/41 |
| 6,843,789 B2 | 1/2005 | Goble | |
| 6,948,503 B2 | 9/2005 | Refior et al. | |
| D574,323 S | 8/2008 | Waaler | |
| 7,844,017 B2 | 11/2010 | Wiss | |
| 7,972,329 B2 | 7/2011 | Refior et al. | |
| 8,114,021 B2 | 2/2012 | Robertson et al. | |
| 8,308,721 B2 | 11/2012 | Shibata et al. | |
| 8,568,411 B2 | 10/2013 | Falkenstein et al. | |
| 8,579,894 B2 | 11/2013 | Falkenstein et al. | |
| 8,685,015 B2 | 4/2014 | Gilbert | |
| 8,915,910 B2 | 12/2014 | Falkenstein et al. | |
| 9,270,202 B2 | 2/2016 | Johnson et al. | |
| 9,283,028 B2 | 3/2016 | Johnson | |
| 9,498,275 B2 | 11/2016 | Wham et al. | |
| 9,498,276 B2 | 11/2016 | Gilbert | |
| 9,504,516 B2 | 11/2016 | Mattmiller et al. | |
| 9,519,021 B2 | 12/2016 | Gilbert | |
| 9,522,032 B2 | 12/2016 | Behnke | |
| 9,559,594 B2 | 1/2017 | Johnson et al. | |
| 9,636,165 B2 | 5/2017 | Larson et al. | |
| 9,642,670 B2 | 5/2017 | Johnson et al. | |
| 9,655,670 B2 | 5/2017 | Larson et al. | |
| 9,705,456 B2 | 7/2017 | Gilbert | |
| 9,770,283 B2 | 9/2017 | Gilbert et al. | |
| 9,770,287 B2 | 9/2017 | Kerr | |
| 9,839,469 B2 | 12/2017 | Gilbert et al. | |
| 9,867,651 B2 | 1/2018 | Wham | |
| 9,872,719 B2 | 1/2018 | Johnson | |
| 9,895,186 B2 | 2/2018 | Gilbert | |
| 10,058,374 B2 | 8/2018 | Wham | |
| 10,130,412 B2 | 11/2018 | Wham | |
| 10,285,750 B2 | 5/2019 | Coulson et al. | |
| 2004/0167508 A1 | 8/2004 | Wham et al. | |
| 2012/0078139 A1 | 3/2012 | Aldridge et al. | |
| 2014/0276754 A1 | 9/2014 | Gilbert et al. | |
| 2015/0025521 A1 | 1/2015 | Friedrichs et al. | |
| 2015/0025523 A1 | 1/2015 | Friedrichs et al. | |
| 2015/0316587 A1 | 11/2015 | Dionne et al. | |

FOREIGN PATENT DOCUMENTS

| | | | |
|---|---|---|---|
| DE | 1099658 B | 2/1961 | |
| DE | 1139927 B | 11/1962 | |
| DE | 1149832 B | 6/1963 | |
| DE | 1439302 A1 | 1/1969 | |
| DE | 2439587 A1 | 2/1975 | |
| DE | 2455174 A1 | 5/1975 | |
| DE | 2407559 A1 | 8/1975 | |
| DE | 2602517 A1 | 7/1976 | |
| DE | 2504280 A1 | 8/1976 | |
| DE | 2540968 A1 | 3/1977 | |
| DE | 2820908 A1 | 11/1978 | |
| DE | 2803275 A1 | 8/1979 | |
| DE | 2823291 A1 | 11/1979 | |
| DE | 2946728 A1 | 5/1981 | |
| DE | 3143421 A1 | 5/1982 | |
| DE | 3045996 A1 | 7/1982 | |
| DE | 3120102 A1 | 12/1982 | |
| DE | 3510586 A1 | 10/1986 | |
| DE | 3604823 A1 | 8/1987 | |
| DE | 3904558 A1 | 8/1990 | |
| DE | 3942998 A1 | 7/1991 | |
| DE | 4206433 A1 | 9/1993 | |
| DE | 4339049 A1 | 5/1995 | |
| DE | 19506363 A1 | 8/1996 | |
| DE | 19717411 A1 | 11/1998 | |
| DE | 19848540 A1 | 5/2000 | |
| DE | 102008058737 A1 | 4/2010 | |
| EP | 0246350 A1 | 11/1987 | |
| EP | 0267403 A2 | 5/1988 | |
| EP | 0296777 A2 | 12/1988 | |
| EP | 0310431 A2 | 4/1989 | |
| EP | 0325456 A2 | 7/1989 | |
| EP | 0336742 A2 | 10/1989 | |
| EP | 0390937 A1 | 10/1990 | |
| EP | 0556705 A1 | 8/1993 | |
| EP | 0608609 A2 | 8/1994 | |
| EP | 0836868 A2 | 4/1998 | |
| EP | 0862060 A2 | 9/1998 | |
| EP | 0862060 A2 * | 9/1998 | ............ G01R 19/02 |
| EP | 0880220 A2 | 11/1998 | |
| EP | 0882955 A1 | 12/1998 | |
| EP | 1051948 A2 | 11/2000 | |
| EP | 1366724 A1 | 12/2003 | |
| EP | 1776929 A1 | 4/2007 | |
| EP | 2680016 A2 * | 1/2014 | ......... A61B 18/1206 |
| EP | 2680016 A2 | 1/2014 | |
| EP | 2898847 A1 | 7/2015 | |
| FR | 1275415 A | 11/1961 | |
| FR | 1347865 A | 1/1964 | |
| FR | 2313708 A1 | 12/1976 | |
| FR | 2364461 A1 | 4/1978 | |
| FR | 2502935 A1 | 10/1982 | |
| FR | 2517953 A1 | 6/1983 | |
| FR | 2573301 A1 | 5/1986 | |
| JP | 63005876 | 1/1988 | |
| JP | 2002065690 A | 3/2002 | |
| JP | 2005185657 A | 7/2005 | |
| SU | 166452 | 11/1964 | |
| SU | 727201 A2 | 4/1980 | |
| WO | 9308756 A1 | 5/1993 | |
| WO | 96/39088 A1 | 12/1996 | |
| WO | 0211634 A1 | 2/2002 | |
| WO | 0245589 A2 | 6/2002 | |
| WO | 03090635 A1 | 11/2003 | |
| WO | 2006050888 A1 | 5/2006 | |
| WO | 2008053532 A1 | 5/2008 | |
| WO | 2012110996 A2 | 8/2012 | |
| WO | WO-2012110996 A2 * | 8/2012 | ............ A61B 18/14 |

OTHER PUBLICATIONS

Vallfors et al., "Automatically Controlled Bipolar Electrosoagulation-'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

"Electrosurgical Unit Analyzer ESU-2400 Series User Manual" Apr. 1, 2002; Retrieved from Internet: <URL:http://www.bcgroupintl.

(56) References Cited

OTHER PUBLICATIONS com/ESU_2400/Updates/ESU-2400_UM_Rev04.pdf>, pp. 6, 11, 73.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence" Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51: (1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences—Yingyong Kexue Xuebao, Shangha CN, vol. 23 No.2;(Mar. 2005); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

U.S. Appl. No. 10/406,690 dated Apr. 3, 2003 inventor: Behnke.

U.S. Appl. No. 10/573,713 dated Mar. 28, 2006 inventor: Wham.

U.S. Appl. No. 11/242,458 dated Oct. 3, 2005 inventor: Becker.

European Search Report issued in application No. EP14200059, dated Aug. 24, 2015.

European Office Action dated Apr. 12, 2018 and issued in corresponding European Patent Application No. 14200059.5, 7 pages.

\* cited by examiner

SYSTEMS AND METHODS FOR CALCULATING TISSUE IMPEDANCE IN ELECTROSURGERY

CROSS REFERENCE TO RELATED APPLICATION

The present application is a divisional of U.S. application Ser. No. 14/562,907, filed on Dec. 8, 2014, which claims the benefit of and priority to U.S. Provisional Application Ser. No. 61/975,070 filed on Apr. 4, 2014, the entire contents of which are incorporated herein by reference.

FIELD

The present technology relates to electrosurgery. In particular, the present disclosure relates to systems and methods for efficiently calculating tissue impedance in electrosurgery.

BACKGROUND

Electrosurgery involves the application of high-frequency electric current to cut or modify biological tissue during an electrosurgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz (kHz) to avoid muscle and/or nerve stimulation.

During electrosurgery, the AC generated by the electrosurgical generator is conducted through tissue disposed between the active and return electrodes. The tissue's impedance converts the electrical energy (also referred to as electrosurgical energy) associated with the AC into heat, which causes the tissue temperature to rise. The electrosurgical generator controls the heating of the tissue by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, usually causing current to flow through a small amount of tissue. In monopolar electrosurgery, the return electrode is located elsewhere on the patient's body and is typically not a part of the electrosurgical instrument itself. In monopolar electrosurgery, the return electrode is part of a device usually referred to as a return pad.

An electrosurgical generator includes a controller that controls the power applied to the tissue over some period of time. The power applied to the tissue may be controlled based on the average power applied to the tissue and the impedance of the tissue, which may be calculated by performing complex computations, e.g., by applying the Goertzel algorithm, on measurements of the voltage and current. These complex computations, however, are computationally intensive and thus require a significant amount of processing power from the controller's digital signal processor.

SUMMARY

The electrosurgical generator and methods of the present disclosure determine the power actually applied to patient's tissue by applying averaging filters to electrical measurements at a desired frequency or over a narrow bandwidth of frequencies. The averaging filters have low computational complexity and may be implemented using commonly available microprocessors, field programmable gate arrays (FPGAs), digital signal processors (DSPs), application specific integrated circuits (ASICs), or programmable DSPs.

In one aspect, the present disclosure features an electrosurgical generator that includes an output stage, a plurality of sensors, and a controller. The output stage is configured to generate electrosurgical energy and the plurality of sensors are configured to sense voltage and current waveforms of the generated electrosurgical energy. The controller is coupled to the output stage and the plurality of sensors, and includes a signal processor and an output controller. The signal processor determines a root mean square (RMS) voltage, an RMS current, an average power, and a real part of an impedance based on the voltage waveform and the current waveform using a plurality of averaging filters. The output controller controls the output stage based on at least one of the RMS voltage, the RMS current, the average power, and the real part of the impedance.

In some embodiments, the signal processor generates a squared voltage waveform, a squared current waveform, and a power waveform. Next, the averaging filters are used to average the squared voltage waveform, the squared current waveform, and the power waveform. Then, the signal processor calculates the RMS voltage, the RMS current, and the average power. The signal processor also calculates a real part of an impedance.

In some embodiments, the electrosurgical generator further includes analog-to-digital (A/D) converters electrically coupled to the current and voltage sensors. The A/D converters sample the sensed voltage waveform and the sensed current waveform to obtain a predetermined number of samples of the sensed voltage and current waveforms.

In some embodiments, the plurality of averaging filters are identical to each other. The plurality of averaging filters may include a cascaded integrator comb (CIC) filter, a boxcar averaging filter, a finite impulse response (FIR) filter, or an infinite impulse response (IIR) filter. The plurality of averaging filters may be low pass filters. The plurality of averaging filters may operate synchronously over a same predetermined number of samples of each of the voltage waveform and the current waveform.

In some embodiments, the output controller generates a feedback signal based on a difference between the real part of the impedance and a desired real part of the impedance. The feedback signal may be used to control the output stage. This impedance control may be utilized for vessel sealing.

The present disclosure, in another aspect, features a method of controlling an electrosurgical generator. The method includes generating electrosurgical energy, sensing a voltage waveform and a current waveform of the generated electrosurgical energy, processing the sensed voltage waveform and the sensed current waveform using a plurality of averaging filters to determine a Root Mean Square (RMS) voltage, an RMS current, an average power, and a real part of an impedance, and controlling the electrosurgical energy based on at least one of the RMS current, the RMS voltage, the average power, and the real part of the impedance.

In some embodiments, processing the voltage waveform and the current waveform includes squaring the sensed voltage waveform, squaring the sensed current waveform, multiplying the sensed voltage waveform and the sensed current waveform to obtain a power waveform, averaging the squared voltage waveform, averaging the squared current waveform, averaging the power waveform to obtain the average power, calculating the RMS voltage based on the average voltage waveform, calculating the RMS current based on the average current waveform, and calculating the real part of the impedance based on the average power and the RMS current.

In other embodiments, processing the voltage waveform and the current waveform further includes sampling the sensed voltage waveform and the sensed current waveform to obtain a predetermined number of samples of the sensed voltage waveform and the sensed current waveform.

In some embodiments, controlling the electrosurgical energy includes generating a feedback signal based on a difference between the real part of the impedance and a desired real part of the impedance and controlling the generated electrosurgical energy based on the feedback signal.

The present disclosure, in yet another aspect, features a processor that performs a method for controlling an electrosurgical generator. The processor may be implemented by a field programmable gate array, an application specific integrated circuit, a digital signal processor, or a programmable digital signal processor.

BRIEF DESCRIPTION OF THE DRAWINGS

Various embodiments of the present disclosure are described with reference to the accompanying drawings wherein.

DETAILED DESCRIPTION

The systems and methods according to the present disclosure employ a plurality of computationally-efficient moving average filters to determine RMS voltage, RMS current, average real power, and a real part of the impedance of treated tissue, which are used as feedback to accurately control the application of RF energy to a patient during an electrosurgical procedure. Since the moving average filters are not frequency dependent, the systems and methods according to the present disclosure are less complex and are more computationally efficient. By employing the moving average filters, sample-by-sample computations are made possible thereby enabling precise controls in real-time. Further, by using the real part of the impedance of the treated tissue, the systems and methods according to the present disclosure are substantially more computationally efficient because they do not need to employ computations that account for parasitic effects in the cables or equipment.

Figure 1:
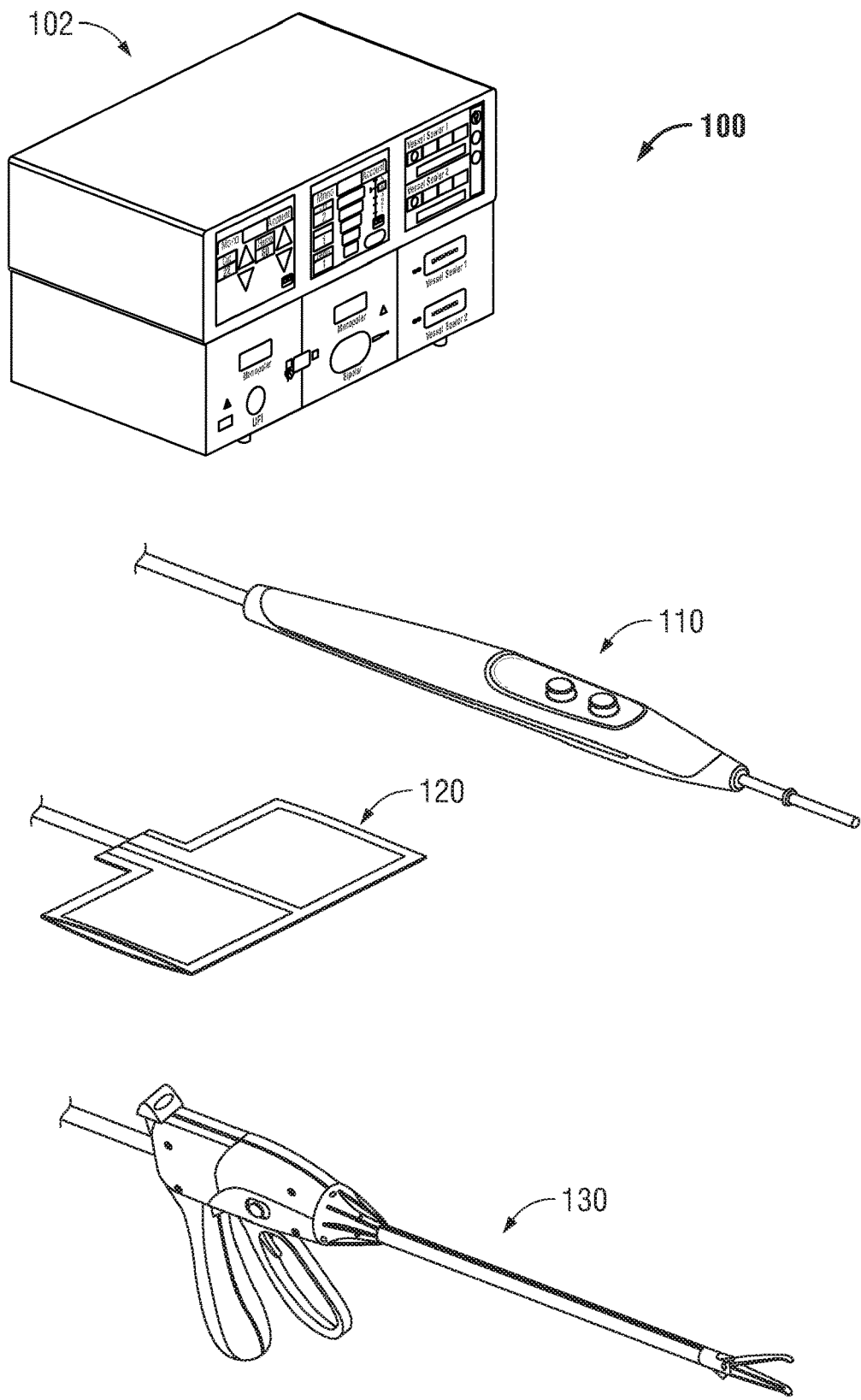
FIG. 1 is an illustration of an electrosurgical system in accordance with embodiments of the present disclosure.

FIG. 1 illustrates an electrosurgical system 100 in accordance with embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the electrosurgical energy. The electrosurgical system 100 may also include a plurality of output connectors corresponding to a variety of electrosurgical instruments.

The electrosurgical system 100 further includes a monopolar electrosurgical instrument 110 having an electrode for treating tissue of the patient (e.g., an electrosurgical cutting probe or ablation electrode, also known as an electrosurgical pencil) with a return pad 120. The monopolar electrosurgical instrument 110 can be connected to the electrosurgical generator 102 via one of the plurality of output connectors. The electrosurgical generator 102 may generate electrosurgical energy in the form of radio frequency (RF) energy. The electrosurgical energy is supplied to the monopolar electrosurgical instrument 110, which applies the electrosurgical energy to treat the tissue. The electrosurgical energy is returned to the electrosurgical generator 102 through the return pad 120. The return pad 120 provides a sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the plurality of output connectors. The electrosurgical energy is supplied to one of the two forceps, is applied to treat the tissue, and is returned to the electrosurgical generator 102 through the other forceps.

The electrosurgical generator 102 may be any suitable type of generator and may include a plurality of connectors to accommodate various types of electrosurgical instruments (e.g., monopolar electrosurgical instrument 110 and bipolar electrosurgical instrument 130). The electrosurgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. For example, when an electrosurgical instrument 110 is connected to the electrosurgical generator 102, the switching mechanism switches the supply of RF energy to the monopolar plug. In embodiments, the electrosurgical generator 102 may be configured to provide RF energy to a plurality instruments simultaneously.

The electrosurgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 110 and 130 may also include a plurality of user controls. In addition, the electrosurgical generator 102 may include one or more display screens for displaying a variety of information related to operation of the electrosurgical generator 102 (e.g., intensity settings and treatment complete indicators).

Figure 2:
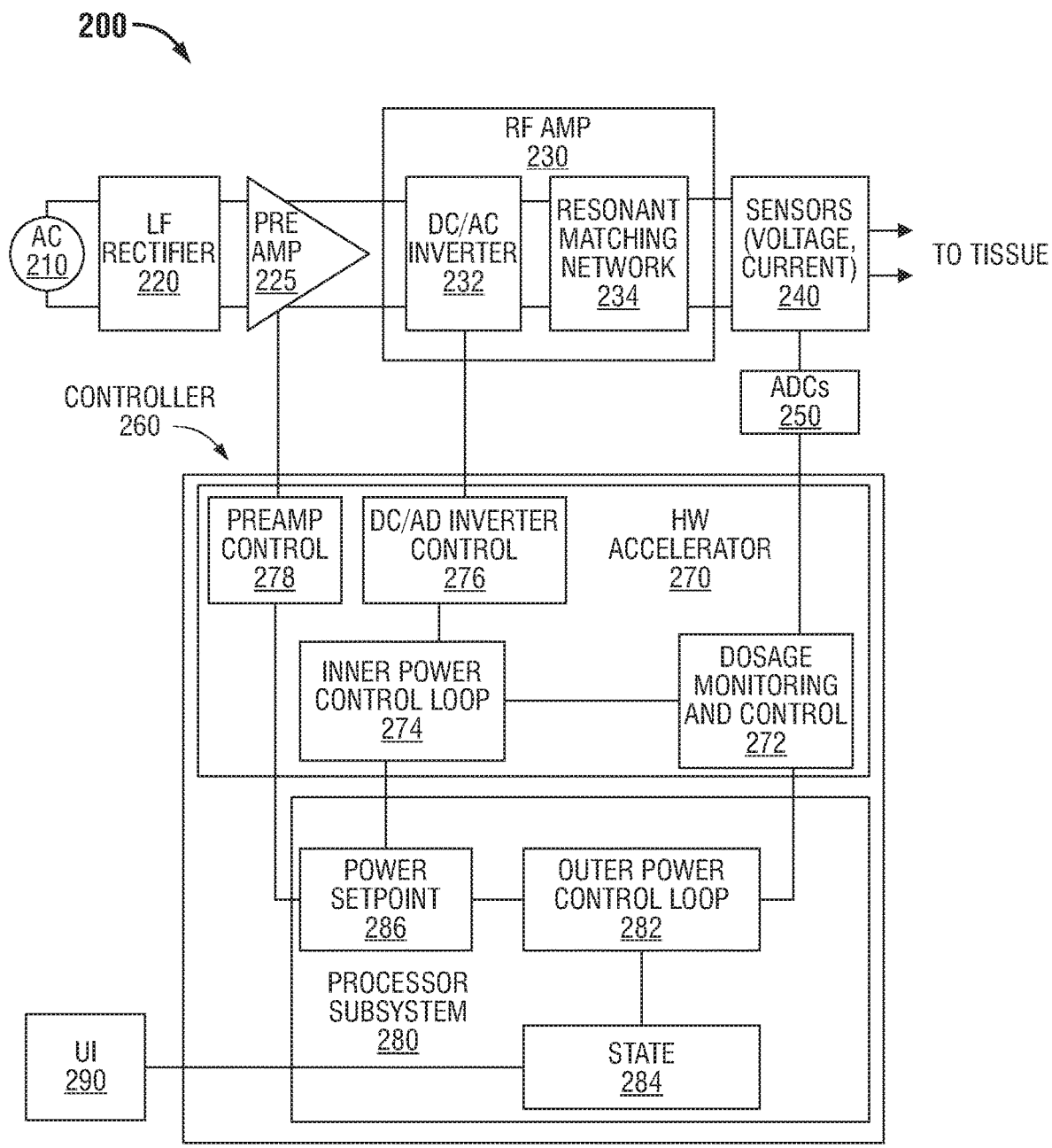
FIG. 2 is a block diagram of circuitry within an electrosurgical generator of the electrosurgical system of FIG. 1.

FIG. 2 is a block diagram of circuitry 200 within the electrosurgical generator 102 of FIG. 1. The generator circuitry 200 includes a low frequency (LF) rectifier 220, a preamplifier 225, an RF amplifier 230, a plurality of sensors 240, analog-to-digital converters (ADCs) 250, a controller 260, a hardware accelerator 270, a processor subsystem 280, and a user interface (UI) 290. The generator circuitry 200 is configured to connect to an alternating current (AC) power source 210, such as a wall power outlet or other power outlet, which generates AC having a low frequency (e.g., 25 Hz, 50 Hz, or 60 Hz). The AC power source 210 provides AC power to the LF rectifier 220, which converts the AC to direct current (DC).

The direct current (DC) output from the LF rectifier 220 is provided to the preamplifier 225 which amplifies the DC to a desired level. The amplified DC is provided to the RF amplifier 230, which includes a direct current-to-alternating current (DC/AC) inverter 232 and a resonant matching network 234. The DC/AC inverter 232 converts the amplified DC to an AC waveform having a frequency suitable for an electrosurgical procedure (e.g., 472 kHz, 29.5 kHz, and 19.7 kHz).

The appropriate frequency for the electrosurgical energy may differ based on electrosurgical procedures and modes of electrosurgery. For example, nerve and muscle stimulations cease at about 100,000 cycles per second (100 kHz) above which point some electrosurgical procedures can be performed safely, i.e., the electrosurgical energy can pass through a patient to targeted tissue with minimal neuromuscular stimulation. For example, typically ablation procedures use a frequency of 472 kHz. Other electrosurgical procedures can be performed at frequencies lower than 100 kHz, e.g., 29.5 kHz or 19.7 kHz, with minimal risk of damaging nerves and muscles. The DC/AC inverter 232 can output AC signals with various frequencies suitable for electrosurgical operations.

As described above, the RF amplifier 230 includes a resonant matching network 234. The resonant matching network 234 is coupled to the output of the DC/AC inverter 232 to match the impedance at the DC/AC inverter 232 to the impedance of the tissue so that there is maximum or optimal power transfer between the generator circuitry 200 and the tissue.

The electrosurgical energy provided by the DC/AC inverter 232 of the RF amplifier 230 is controlled by the controller 260. The voltage and current waveforms of the electrosurgical energy output from the DC/AC inverter 232 are sensed by the plurality of sensors 240 and provided to the controller 260, which generates control signals to control the output of the preamplifier 225 and the output of the DC/AC inverter 232. The controller 260 also receives input signals via the user interface (UI) 290. The UI 290 allows a user to select a type of electrosurgical procedure (e.g., monopolar or bipolar) and a mode (e.g., coagulation, ablation, sealing, or cutting), or input desired control parameters for the electrosurgical procedure or the mode.

The plurality of sensors 240 sense voltage and current at the output of the RF amplifier 230. The plurality of sensors 240 may include two or more pairs or sets of voltage and current sensors that provide redundant measurements of the voltage and current. This redundancy ensures the reliability, accuracy, and stability of the voltage and current measurements at the output of the RF amplifier 230. In embodiments, the plurality of sensors 240 may include fewer or more sets of voltage and current sensors depending on the application or the design requirements. The plurality of sensors 240 may also measure the voltage and current output from other components of the generator circuitry 200 such as the DC/AC inverter 232 or the resonant matching network 234. The plurality of sensors 240 may include any known technology for measuring voltage and current including, for example, a Rogowski coil.

The sensed voltage and current waveforms are fed to analog-to-digital converters (ADCs) 250. The ADCs 250 sample the sensed voltage and current waveforms to obtain digital samples of the voltage and current waveforms. The digital samples of the voltage and current waveforms are processed by the controller 260 and used to generate control signals to control the DC/AC inverter 232 of the RF amplifier 230 and the preamplifier 225. The ADCs 250 may be configured to sample the sensed voltage and current waveforms at a sample period that is an integer multiple of the RF frequency.

As shown in FIG. 2, the controller 260 includes a hardware accelerator 270 and a processor subsystem 280. As described above, the controller 260 is also coupled to a UI 290, which receives input commands from a user and displays input and output information related to characteristics of the electrosurgical energy (e.g., selected power level). The hardware accelerator 270 processes the output from the ADCs 250 and cooperates with the processor subsystem 280 to generate control signals.

The hardware accelerator 270 includes a dosage monitoring and control (DMAC) 272, an inner power control loop 274, a DC/AC inverter controller 276, and a preamplifier controller 278. All or a portion of the controller 260 may be implemented by a field programmable gate array (FPGA), an application specific integrated circuit (ASIC), a digital signal processor (DSP), and/or a microcontroller.

The DMAC 272 receives samples of the voltage and current waveforms from the ADCs 250 and calculates the average real power, the RMS voltage, the RMS current, and the real part of the impedance of the tissue, as described in greater detail below. The DMAC 272 then provides the average real power, the RMS voltage, the RMS current, and the real part of the impedance of the tissue to the inner power control loop 274, which generates a control signal for the DC/AC inverter controller 276 based on one or more of the average real power, the RMS voltage, the RMS current, and the real part of the impedance of the tissue. The DC/AC inverter controller 276 in turn generates a first pulse-width modulation (PWM) control signal to control the output of the DC/AC inverter 232.

The processor subsystem 280 includes an outer power control loop 282, a state machine 284, and a power setpoint circuit 286. The processor subsystem 280 generates a second PWM control signal based on the output of the DMAC 272 and parameters (e.g., electrosurgical mode) selected by the user via the UI 290. The parameters selected by the user are provided to the state machine 284, which determines a state or mode of the electrosurgical generator 102. The outer power control loop 282 uses this state information and the output from the DMAC 272 to determine control data. The control data is provided to the power setpoint circuit 286, which generates a power setpoint based on the control data. The preamplifier controller 278 uses the power setpoint to generate an appropriate PWM control signal for controlling the preamplifier 225 to amplify the DC output from the LF rectifier 220 to a desired level. If the user does not provide operational parameters to the state machine 284 via the UI 290, then the state machine 284 may enter and maintain a default state.

Figure 3:
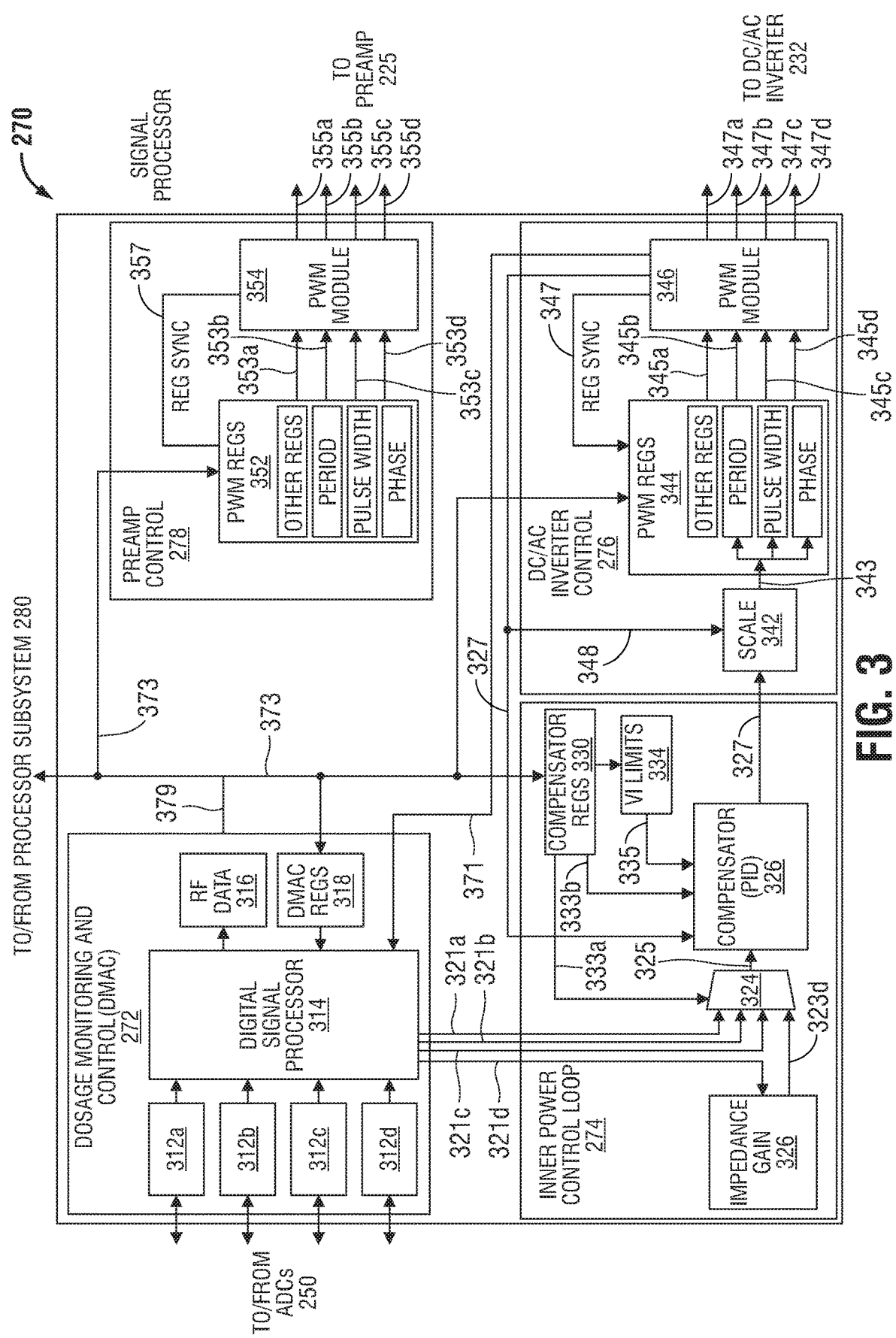
FIG. 3 is a schematic diagram of a controller of the generator of FIG. 2.

FIG. 3 shows a more detailed diagram of the hardware accelerator 270 of FIG. 2. The hardware accelerator 270 implements those functions of the generator circuitry 200 that may have special processing requirements such as high processing speeds. The hardware accelerator 270 includes the DMAC 272, the inner power loop control 274, the DC/AC inverter controller 276, and the preamplifier controller 278 shown in FIG. 2.

The DMAC 272 includes four analog-to-digital converter (ADC) controllers 312a-312d, a digital signal processor 314, an RF data registers 316, and DMAC registers 318. The ADC controllers 312a-312d control the operation of the ADCs 250, which convert sensed voltage and current waveforms into digital data. The digital data is then provided to the digital signal processor 314 that implements various filtering and other digital signal processing functions, some of which are described in more detail below.

The sensed voltage and current are input to the ADCs 250, which sample the sensed voltage and current. The ADC controllers 312a-312d provide operational parameters, including a predetermined sampling rate, to the ADCs 250 so that the ADCs sample the sensed voltage and current synchronously at a predetermined sampling rate, i.e., a predetermined number of samples per second, or predetermined sampling period. The ADC controllers 312a-312d may be configured to control the ADCs 250 so that the sampling period corresponds to an integer multiple of the RF frequency of the voltage and current waveforms.

The digital data obtained by sampling the voltage and current waveforms is provided to the digital signal processor 314 via the ADC controllers 312a-312d. The digital signal processor 314 uses the digital data to calculate RMS voltage ($V_{rms}$), RMS current ($I_{rms}$), average real power ($P_{avg}$), and the real part of the impedance $Z_{re}$. The RMS voltage and RMS current are calculated according to the following equations:

$$V_{rms} = \sqrt{\operatorname{avg}(V^2)} \quad (1)$$

$$I_{rms} = \sqrt{\operatorname{avg}(I^2)}, \quad (2)$$

where V represents the samples of the voltage waveform, I represents samples of the current waveform, and "avg( )" represents an averaging function. The digital signal processor 314 uses averaging filters in calculating an average value of the real power. The average real power $P_{avg}$ and the real part of the impedance $Z_{re}$ are then calculated according to the following equations:

$$P_{avg} = \operatorname{avg}(V_{rms} \times I_{rms}) \quad (3)$$

$$Z_{re} = \frac{V_{rms}}{I_{rms}} \times \cos \varphi, \quad (4)$$

where φ is the phase angle between the sampled voltage and current waveforms. Another equation for determining the impedance is:

$$Z = \frac{V^2}{P}, \quad (5)$$

where P is power. Because $V = V_{rms} \times \cos \varphi$, the equation for the real part of the impedance becomes:

$$Z_{real} = \frac{(V_{rms} \times \cos \varphi)^2}{P_{avg}}. \quad (6)$$

Combining equations (4) and (6) leads into the following equality:

$$\frac{(V_{rms} \times \cos \varphi)^2}{P_{avg}} = \frac{V_{rms}}{I_{rms}} \times \cos \varphi. \quad (7)$$

Solving equation (7) for cos ω results in the equation:

$$\cos \varphi = \frac{P_{avg}}{(V_{rms} \times I_{rms})}. \quad (8)$$

Substituting equation (8) into equation (4) results in the equation:

$$Z_{real} = \frac{P_{avg}}{I_{rms}^2}. \quad (9)$$

The digital signal processor 314 calculates the real part of the impedance by first calculating the RMS current and the average real power as described above and then dividing the average real power by the squared RMS current by using equations (1), (2), and (9).

As shown above, equations (1)-(3), (8), and (9) do not require computations of the phase component φ, i.e., the phase difference between the voltage and current phasors. Thus, the digital signal processor 314 does not need to perform Fourier transformations, digital Fourier transformations, or fast Fourier transformations, or some other transformation requiring complex phase computations. Instead, the digital signal processor 314 implements a plurality of averaging filters, which are described in more detail below. In this way, the systems and methods according to the present disclosure significantly reduce computational complexity and enable real-time control.

The output of the digital signal processor 314 is provided to the processor subsystem 280 of FIG. 2 via RF data registers 316. The DMAC 272 also includes DMAC registers 318 that receive and store relevant parameters for the digital signal processor 314. The digital signal processor 314 further receives signals from a PWM module 346 of the DC/AC inverter controller 276. The RF data registers 316 contain RMS voltage values, RMS current values, and real average power values, which are used as feedback for the hardware accelerator 270 to provide voltage, current, or power control based on which control mode is active. The contents of the RF data registers 316 are also passed on to the processor sub-system 280. The DMAC registers 318 provide the interface between the DMAC digital signal processor 314 and the processor subsystem 280. The DMAC registers 318 provide setup information such as the sensor comparison delta limits, high pass filter coefficients, and sensor scale factors (calibration coefficients). The information provided to the compensator registers 330 may include proportional, integral, and derivative gain coefficients, and voltage-current limits for the compensator (PID) 326.

The DMAC 272 provides control signals to the inner power control loop 274 via signal lines 321a-321d and to the processor subsystem 280 via signal line 379 (FIG. 3). As shown in FIG. 2, the inner power control loop 274 processes the control signals and outputs a control signal to the DC/AC inverter controller 276. The inner power control loop 274 includes an impedance gain block 322, a multiplexer 324, a compensator 326, compensator registers 330, and VI limiter 334. The impedance gain block 322 receives the real part of the impedance via a signal line 321d, amplifies it to a desired level, and provides the amplified real part of the impedance to the compensator 326 via signal line 323d.

The impedance gain block 322 uses the impedance and optionally other parameters to linearize the inverter plant gain for control purposes. For optimal control system performance, a consistent or constant gain is maintained across the range of operation so that the stability margin, also known as gain and phase margin, is consistent or constant across the range of operation. A gain scheduling approach may be used to linearize the gain based on the impedance and other parameters.

The multiplexer 324 receives the RMS voltage, the RMS current, and the average real power via signal lines 321a-321c. The multiplexer 324 also receives a select control signal which selects one of the inputs (i.e., the RMS voltage, the RMS current, and the average real power) from the compensator registers 330 and provides the selected input to the compensator 326. Thus, the digital signal processor 314 of the DMAC 272 generates control signals, which include the RMS voltage, the RMS current, the average real power, and the real part of the impedance, and provides them to the multiplexer 324 and the impedance gain block 322 of the inner power control loop 274 via signal lines 321a-321d, respectively.

When there is a user input, the processor subsystem 280 receives the user input and processes it with the outputs from the digital signal processor 314 via signal line 379. The processor subsystem 280 provides control signals via compensator registers 330 to VI limiter 334, which corresponds to the power setpoint circuit 286 in FIG. 2. The VI limiter 334 then provides a desired power profile (e.g., a minimum and a maximum limits of the power for a set electrosurgical mode or operation) to the compensator 326 based on the user input and the output of the digital signal processor 314. The compensator registers 330 also provide other control parameters to the compensator 326, and then the compensator 326 combines all control parameters from the compensator registers 330, the VI limiter 334, the multiplexer 324, and the impedance gain block 322 to generate an output to the DC/AC inverter controller 276 via signal line 327.

The DC/AC inverter controller 276 receives control parameters and outputs control signals that drive the DC/AC inverter 232. The DC/AC inverter controller 276 includes scale unit 342, PWM registers 344, and the PWM module 346. The scale unit 342 scales the output of the compensator 326 based on a signal received from the PWM module 346 via signal line 347. This signal may be in units of normalized C phase, which directly drives the relative periods of the PWM signals 347a-347d. The PWM registers 344 store PWM-related parameters to control the DC/AC inverter 232, e.g., a period, a pulse width, and a phase of the AC signal to be generated by the DC/AC inverter 232 and other related parameters. The PWM module 346 receives output from the PWM registers 344 and generates four control signals, 347a-347d, that control four transistors (not shown) of the DC/AC inverter 232 of the RF amplifier 230 in FIG. 2. The PWM module 346 also synchronizes its information with the information in the PWM registers 344 via a register sync signal 347.

The PWM module 346 further provides control signals to the compensator 326 of the inner power control loop 274. The processor subsystem 280 determines when control is applied and provides control signals to the inner power control loop 274 and the DC/AC inverter control block 276. The DMAC subsystem 272 provides processed parameters, such as RMS voltage values, RMS current values, and real average power values, to the compensator 326 of the inner power control loop 274.

In some embodiments, the processor subsystem 280 may send the control signals to the preamplifier controller 278 via signal line 373. The preamplifier controller 278 processes the control signals and generates another control signal so that the preamplifier 225 amplifies direct current (DC) to a desired level suitable for being converted by the RF amplifier 230. The Preamplifier controller 278 includes PWM registers 352 and a PWM module 354. The PWM registers 352 receive outputs from the processor subsystem 280 via signal link 373 and stores relevant parameters in a manner similar to the PWM registers 344. The PWM module 354 also sends a register sync signal to the PWM registers 352 and generates four control signals, 355a-355d, that control four transistors (not shown) of the preamplifier 225 in FIG. 2.

Figure 4:
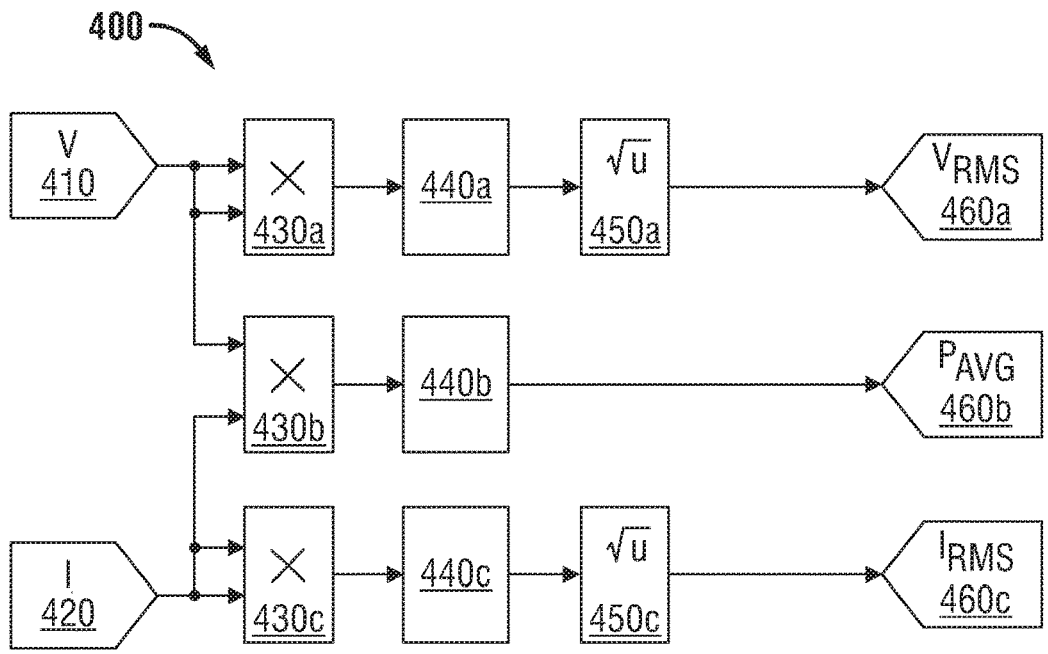
FIG. 4 is a functional block diagram of signal processing functions performed by a digital signal processor of FIG. 2.
Figure 5:
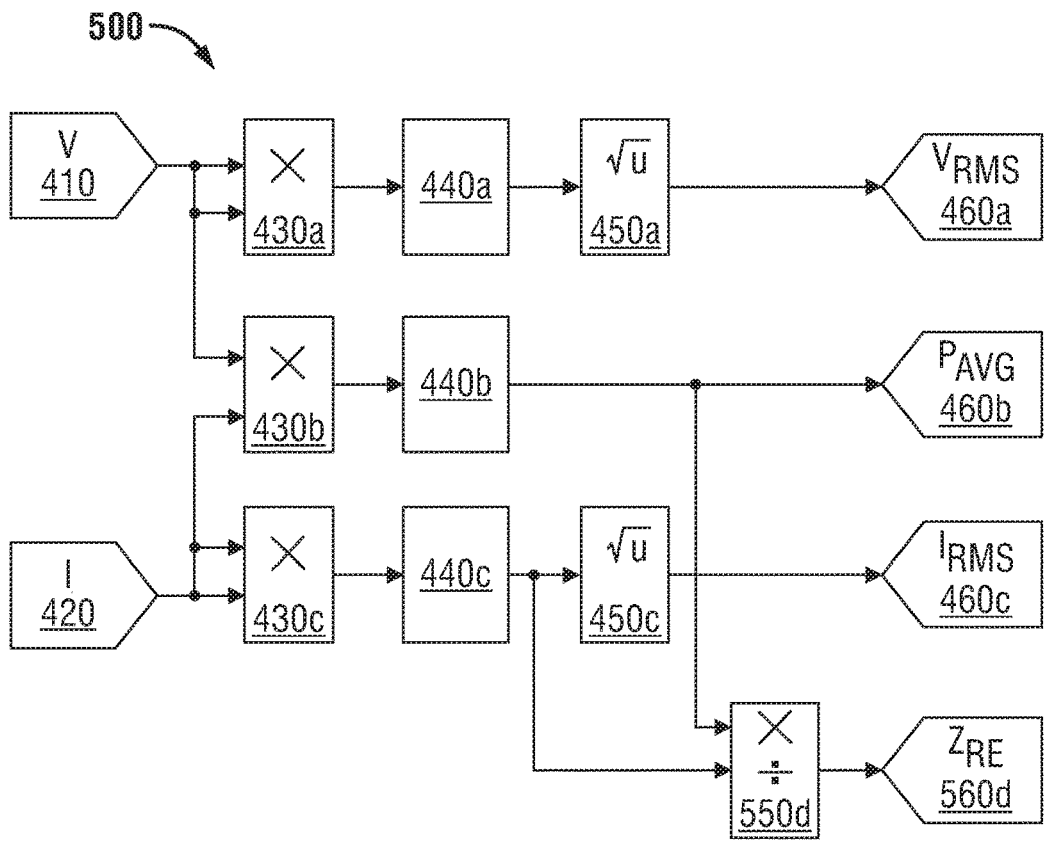
FIG. 5 is a functional block diagram of additional signal processing functions performed by the digital signal processor of FIG. 2.

FIGS. 4 and 5 are functional block diagrams of signal processing functions that are implemented by the digital signal processor 314 of FIG. 3. The signal processing functions include a plurality of multipliers 430a-430c, a plurality of averaging filters 440a-440c, and a plurality of square-root calculators 450a and 450c that process the measured voltage 410 and the measured current 420 to obtain an RMS voltage 460a, an average power 460b, and an RMS current 460c. The multiplier 430a multiplies the measured voltage 410 (V) by itself to obtain a squared voltage value. Similarly, the multiplier 430c multiplies the measured current 420 (I) by itself to obtain a squared current. Lastly, the multiplier 430b multiplies the measured voltage 410 and the measured current 420 to obtain a power value.

The averaging filters 440a-440c average the squared voltage, the squared current, and the power value, respectively, resulting in an average voltage value, an average current value, and an average power value 460b ($P_{AVG}$), respectively. The average power value 460b represents the real average power that is mostly dissipated in the treated tissue. The square-root calculators 450a and 450c calculate square root values of the averaged voltage value and the averaged current value, resulting in the RMS voltage 460a ($V_{RMS}$) and the RMS current 460c ($I_{RMS}$), respectively.

That averaging filters 440a-440c may be implemented using three identical low pass filters operating synchronously over the same number of RF samples obtained by the ADCs 250 described above. The number of RF samples, i.e., the window size, is selected to be equal to an integer number of RF periods. This allows the cascaded integrator-comb (CIC) filters described in the present disclosure to achieve their full potential as averaging filters.

FIG. 5 is a functional block diagram of signal processing functions that implement equation (9) shown above. These signal processing functions are the same as the signal processing functions of FIG. 4 except that the signal processing functions of FIG. 5 include a calculator 550d that calculates the real part of the impedance 560d ($Z_{RE}$). The calculator 550d divides the average power value output from the averaging filter 440b by the average current value output from the averaging filter 440c to calculate the real part of the impedance 560d ($Z_{RE}$).

As shown in FIG. 5, the signal processing functions do not perform frequency-related analysis, e.g., Fourier analysis using the fast Fourier transform (FFT) or the discrete Fourier transform (DFT), on the measured voltage 410 and measured current 420 to determine measured power and impedance values. In particular, the signal processing functions do not employ Goertzel filters, which is an implementation of the DFT. As a result, the signal processing performed by the digital signal processor 314 of FIG. 3 is not as complex as the frequency-based analysis and thus is more computationally efficient.

The plurality of averaging filters 440a-440c are moving average filters. The moving average filters enable real-time control because they measure average values sample by sample. The averaging filters 440a-440c, however, introduce a group delay. The group delay is a measure of time delay. Nevertheless, the averaging filters 440a-440c may be designed in such a way as to make the group delay sufficiently small to result in accurate, real-time feedback to the controller 260.

In order for the averaging filters 440a-440c to perform accurate calculations, all of the averaging filters 440a-440c are designed to be identical to each other with respect to their sampling rates or periods and sample window sizes. The averaging filters 440a-440c may be low-pass filters. The averaging filters 440a-440c may also utilize a cascaded integrator comb (CIC) filter, such as a Boxcar filter.

The specifications of the averaging filters 440a-440c, such as the pass band, the stop band, the pass band ripple, and the stop band attenuation, depend on the characteristics of the desired waveform and the maximum time delay. Examples of different waveform types are shown in Table 1 below:

TABLE 1

| Waveform Group | Waveform Type | RF Duty Cycle | Lowest frequency in RF waveform, KHz | Rep. Rate, µs |
|---|---|---|---|---|
| I | Cut, Ligasure, Bipolar | 100.00% | 472 | 2.1 |
| II | Blend | 50.00% | 29.5 | 33.9 |
|  | Valleylab Mode | 25.00% | 29.5 | 33.9 |
|  | Fulgurate | 6.25% | 29.5 | 33.9 |
| III | Spray | 4.17% | 19.7 | 50.8 |

Each of the different waveform groups, which are differentiated by the lowest frequency in the RF waveform, or each of the different waveform types may have different averaging filters having different specifications. Also, in general, the performance of an averaging filter will improve as the time delay of the averaging filter increases.

If the RF signal output from the electrosurgical generator is a narrowband signal, the Boxcar filter can be used as the averaging filter to suppress all harmonics of the RF signal with the exception of the DC component. This is because all the energy of the RF signal excluding the DC component will map to the nulls of the magnitude response of the Boxcar filter (see, e.g., FIG. 8A). This feature of the Boxcar filter makes it a good choice for implementing the averaging filters 440a-440c. Also, the Boxcar filter is an inexpensive filter to implement and is inherently stable. The Boxcar filter may be designed so that the filter delay is as small as possible and is equal to the period of the RF signal waveform.

Figure 6A:
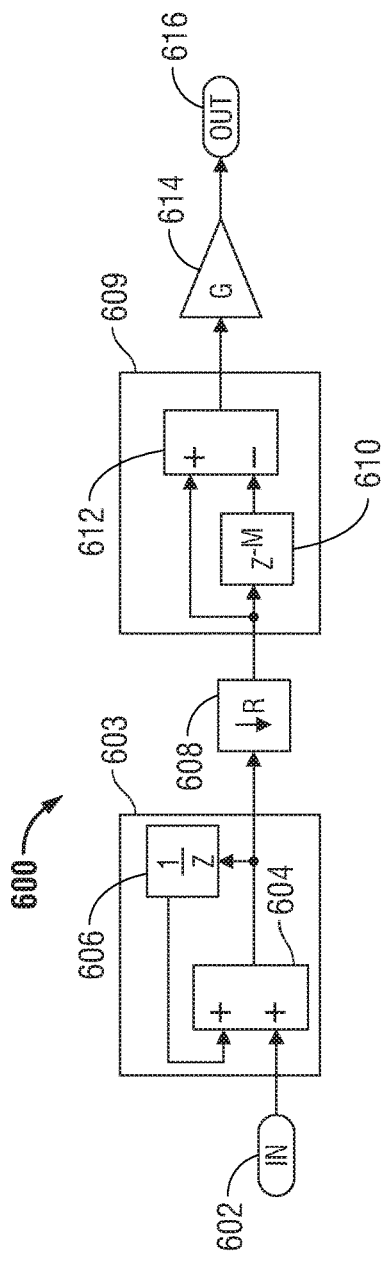
FIGS. 6A and 6B are block diagrams of averaging filters in the form of Boxcar filters in accordance with some embodiments of the present disclosure.

FIG. 6A shows an embodiment of a Boxcar filter 600 that may be used to implement the averaging filters 440a-440c of FIGS. 4 and 5. The Boxcar filter can be represented as a CIC filter, which is a moving average filter. One advantage of the CIC topology is that it provides a more general approach and thus allows for more design flexibility. The two basic building blocks of the CIC filter are an integrator 603 and a comb filter 609, which incorporates a differentiator 612. The Boxcar filter 600 also includes a decimator 608 coupled between the integrator 603 and the comb filter 609, and a gain 614 coupled between the comb filter 609 and the output 616. The Boxcar filter 600, which averages over M samples, can be viewed as a first-order CIC filter having the following parameters: a decimation factor (R) of M, a differential delay (M) of 1, and a number of sections (N) of 1. As described below, these parameters may be adjusted to achieve a desired filter response depending on, for example, the waveform type of the RF signal.

The integrator 603 is a single-pole, infinite impulse response (IIR) filter with a unity feedback coefficient and is generally described by the following difference equation:

$$y[n]=y[n-1]+x[n], \quad (10)$$

where x[n] represents a current input value 602, y[n−1] represents a delayed output value, and y[n] represents the sum of y[n−1] and x[n] and is the output of the integrator 603. The integrator 603 is also referred to as an accumulator. The transfer function for the integrator 603 in the z-domain is:

$$H_1(z) = \frac{1}{1-z^{-1}}. \quad (11)$$

The decimator 608 downsamples the output from the integrator 603 by R and provides the result to the comb filter 609. An important characteristic of the decimator 608 is that the shape of the CIC filter response changes very little. For values of R larger than 16, the change in the filter shape is negligible.

The comb filter 609 includes a differential delay 610 and a differentiator 612. A downsampled output from the integrator 603 is delayed by M by the differential delay 610. The differentiator 612 subtracts a delayed version of the downsampled output from the downsampled output. The comb filter 609 is described by the following difference equation:

$$y[n]=x[n]-x[n-RM], \quad (12)$$

where x[n] represents an input to the comb filter 609, x[n−RM] represents a delayed version of x[n], and y[n] represents the difference between x[n−RM] and x[n], and is the output of the comb filter 609. The transfer function of the comb filter 609 in the z-domain is:

$$H_2(z) = 1 - z^{-RM},$$

where R is the decimation factor and M is the differential delay.

Thus, the transfer function for the Boxcar filter 600 in the z-domain is:

$$H(z) = H_1(z) \times H_2(z) \times G = \frac{1}{1-z^{-1}} \times (1 - z^{-RM}) \times G = G \times \sum_{k=0}^{RM-1} z^{-k}, \quad (13)$$

where G represents a gain value.

Figure 6B:
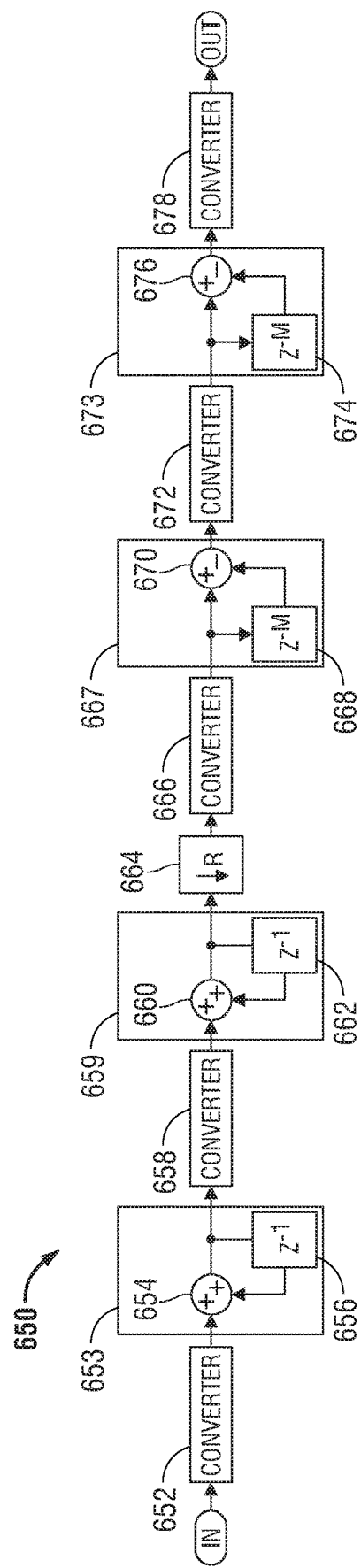

In some embodiments, each of the averaging filters 440a-440c of FIGS. 4 and 5 may be implemented as a second-order CIC Boxcar filter 650 illustrated in FIG. 6B. The Boxcar filter 650 includes a decimator 664, two integrators 653 and 659 that are placed before the decimator 664, and two comb filters 665 and 671 that are placed after the decimator 664. In other embodiments, the second-order CIC filter may be formed by coupling together two first-order CIC filters in series. In yet other embodiments, the second-order CIC filter may include a plurality of integrators coupled together in parallel, a plurality of comb filters coupled together in parallel, and a decimator coupled between the plurality of integrators and the plurality of comb filters.

The Boxcar filter 650 also includes a plurality of converters 652, 658, 666, 672, and 678, which stabilize the inputs to each of the integrators 653 and 659 and Boxcar filters 667 and 673. Specifically, the plurality of converters 652, 658, 666, 672, and 678 are scaling factors to prevent fixed point overflow. When CIC filters are cascaded, the word size grows by one bit per comb filter stage. Each of the plurality of converters 652, 658, 666, 672, and 678 removes the least significant bit (LSB), but may add some noise to the output of the cascaded filter. The transfer function of the Boxcar filter 650 in the z-domain is $$H(z) = \left(\frac{1}{1-z^{-1}}\right)^2 \times (1 - z^{-RM})^2 = \left(\frac{1-z^{-RM}}{1-z^{-1}}\right)^2 = \left(\sum_{k=0}^{RM-1} z^{-k}\right)^2, \quad (14)$$

where M represents a differential delay and R represents a decimator factor. The transfer function is a squared transfer function of the first-order CIC filter 600 because this embodiment of the Boxcar filter incorporates two sets of first-order CIC Boxcar filters.

Figure 7:
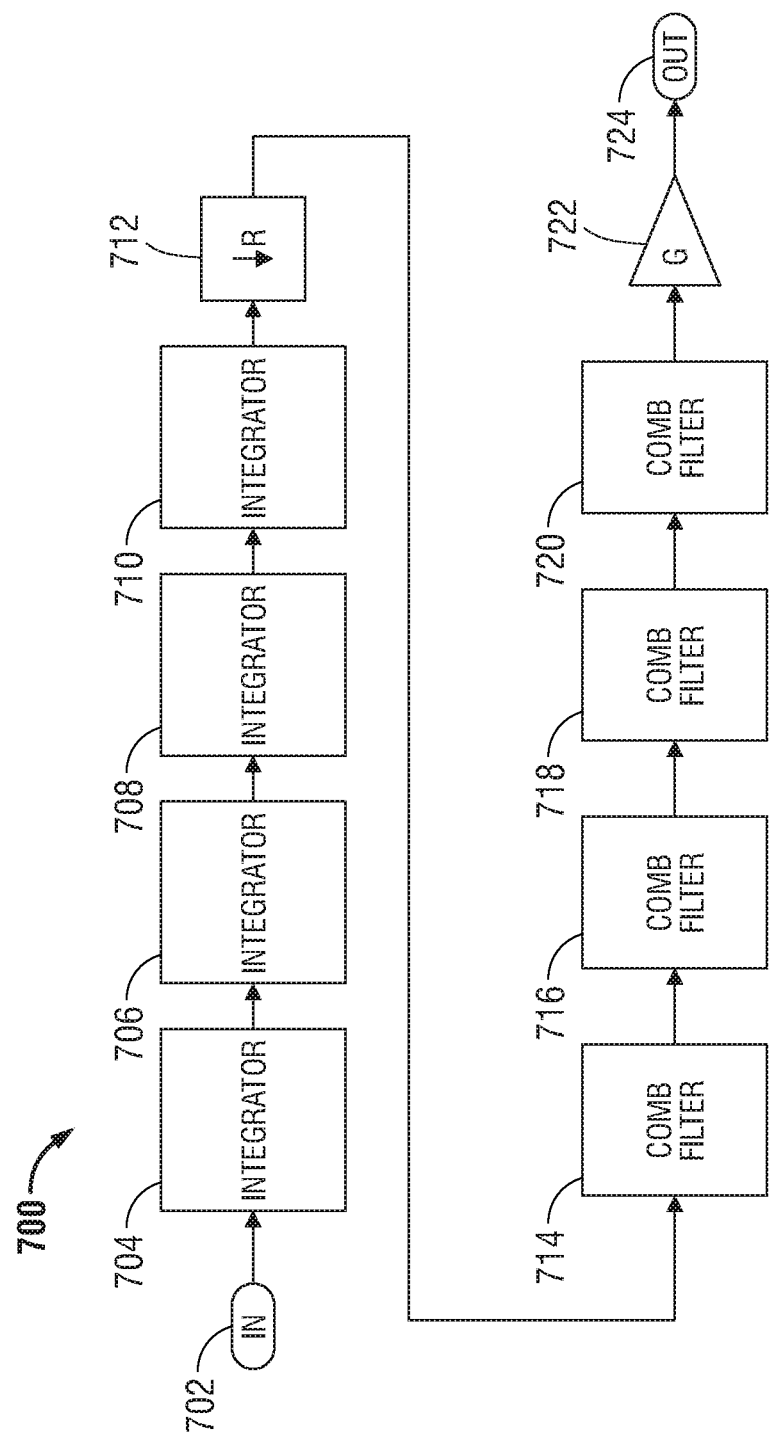
FIG. 7 is a block diagram of an averaging filter in accordance with other embodiments of the present disclosure.

In other embodiments, each of the averaging filters 440a-440c of FIGS. 4 and 5 may be implemented as a fourth-order CIC Boxcar filter 650 illustrated in FIG. 7. The fourth-order Boxcar filter 700 includes four integrators 704, 706, 708, and 710, one decimator 712, and four comb filters 714, 716, 718, and 720, which are also referred to as differentiators. Each integrator 704, 706, 708, and 710 includes an adder and a delay block, and each comb filter includes a differential delay block and a differentiator, similar to the integrators 603, 653, and 659 and comb filters 609, 667, and 673 of FIGS. 6A and 6B. The transfer function of the fourth-order Boxcar filter is:

$$H(z) = \left(\frac{1}{1-z^{-1}}\right)^4 \times (1 - z^{-RM})^4 = \left(\frac{1-z^{-RM}}{1-z^{-1}}\right)^4 = \left(\sum_{k=0}^{RM-1} z^{-k}\right)^4, \quad (15)$$

where M represents a differential delay, R represents a decimator factor, and the power of the transfer function represents the order of the CIC filter.

Additional integrators and comb filters may be added to or removed from the Boxcar filter 700 to obtain a higher-order or lower-order Boxcar filter. Thus, a generalized transfer function is obtained as follows:

$$H(z) = \left(\frac{1}{1-z^{-1}}\right)^N \times (1 - z^{-RM})^N = \left(\frac{1-z^{-RM}}{1-z^{-1}}\right)^N = \left(\sum_{k=0}^{RM-1} z^{-k}\right)^N, \quad (16)$$

where M represents a differential delay, R represents a decimator factor, and N represents the order of the Boxcar filter. Higher-order CIC Boxcar filters provide more accuracy, but increase the group delay.

FIGS. 8A-10B illustrate example frequency and time responses of the averaging filters 440a-440c described above. During surgical procedures, tissue impedance perturbations add some frequency content to the sensed voltage and current waveforms. Thus, the sensed voltage and current waveforms incorporate low frequency noise. The frequency and time responses are based on a sampling frequency of 7,552.075 kHz, a carrier signal of $\sin(2\pi \times 472\ e^3)$, and a tissue impedance perturbation of $0.2 \times \sin(2\pi \times 200\ e^3)$. The carrier signal has a frequency of 472 kHz and the tissue impedance perturbation has a frequency of 200 kHz. Multipliers 430a-430c multiply two sampled waveforms that have the same frequency. Thus, several embodiments of the Boxcar filter in FIGS. 8A-10B receive 944 kHz voltage, current, and power waveforms and a 400 kHz waveform for the tissue impedance perturbation.

Figure 8A:
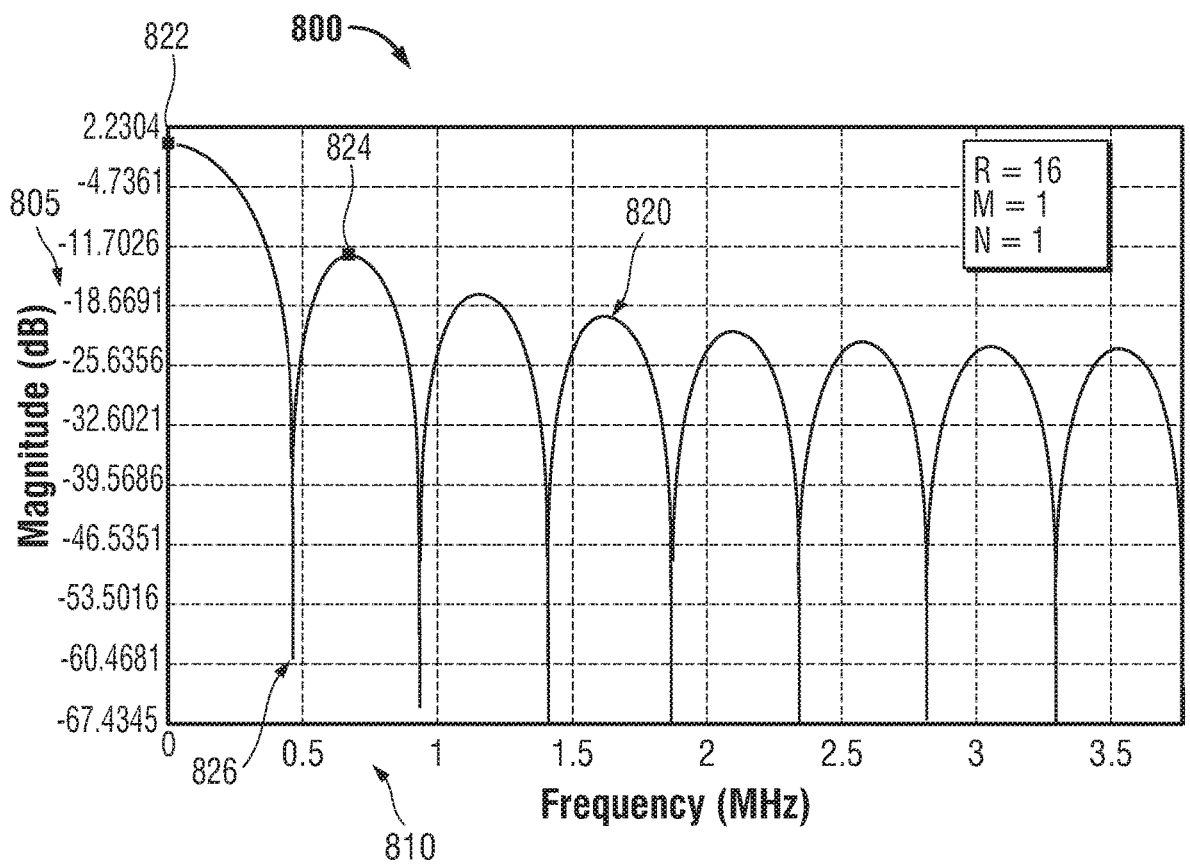
FIGS. 8A and 8B illustrate a frequency domain response and a time domain response, respectively, of the sensed signal in accordance with embodiments of the Boxcar filter of the present disclosure.
Figure 8B:
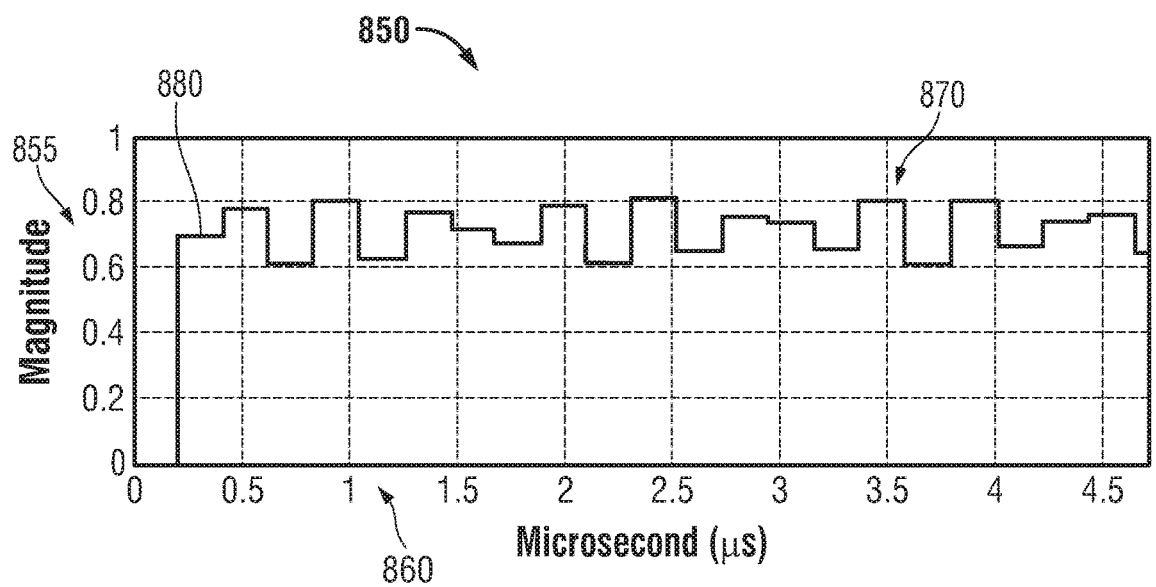

FIG. 8A illustrates the frequency response 800 and FIG. 8B illustrates the time response 850 for a first-order Boxcar filter (i.e., N=1), whose decimator factor is 16 (i.e., R=16), and whose differential delay is 1 (i.e., M=1). In FIG. 8A, the frequency response graph 800 has two axes: a frequency axis 810 indicating the frequency components of the RF signal in MHz and a magnitude axis 805 indicating the magnitude in decibels (dBs) of the frequency components of the RF signal. The frequency response 820 has several lobes (e.g., 822 and 824) and several nulls (e.g., 826). The first lobe 822 is centered at 0 kHz and has a magnitude of 0. The second lobe 824 is centered at 675.7 kHz and has a magnitude of −13.14684 dB. Thus, there is about −13 dB of attenuation in the stop band (i.e., −13 dB from the first lobe to the second lobe. The attenuation may be increased by increasing the number of sections N of the filter as shown in FIG. 6B (two sections) and FIG. 7 (four sections). The nulls between each lobe are a multiple of 472 kHz, which is the original frequency of the carrier so that the carrier signal would be substantially attenuated and would not appear in the signal response in the time domain.

FIG. 8B illustrates a signal response corresponding to the frequency response of FIG. 8A. The signal response graph 850 includes two axes: a time axis 860 in units of microseconds (μs) and a magnitude axis 855. The rise time 880 represents the group delay, which, in this example, is about 0.2 μs. As shown, the signal response 870 oscillates between the magnitudes of 0.6 and 0.8, which indicates that the signal at the output of the filter is noisy.

Referring again to FIG. 8A, the carrier signal has a frequency of 472 kHz and the noise, which is caused by tissue perturbations, has a frequency of 200 kHz. The energy at every multiple of 200 kHz, i.e., 200 kHz, 400 kHz, and etc., has an effect on the signal response 870. Furthermore, sums or differences between energy at multiples of 472 kHz and energy at multiples of 200 kHz also have effects on the signal response 870. The most influential energy is centered at the frequencies of 200 kHz, 272 kHz (472 kHz−200 kHz), and 672 kHz (472 kHz+200 kHz). The energy at these three frequencies are not sufficiently attenuated based on the frequency response graph 800 because they are not near the nulls, and the energy at 672 kHz is aliased into the energy at 272 kHz, thus polluting the signal response 870 with non-real energy. This noise may be reduced by increasing the order of the Boxcar filter.

Figure 9A:
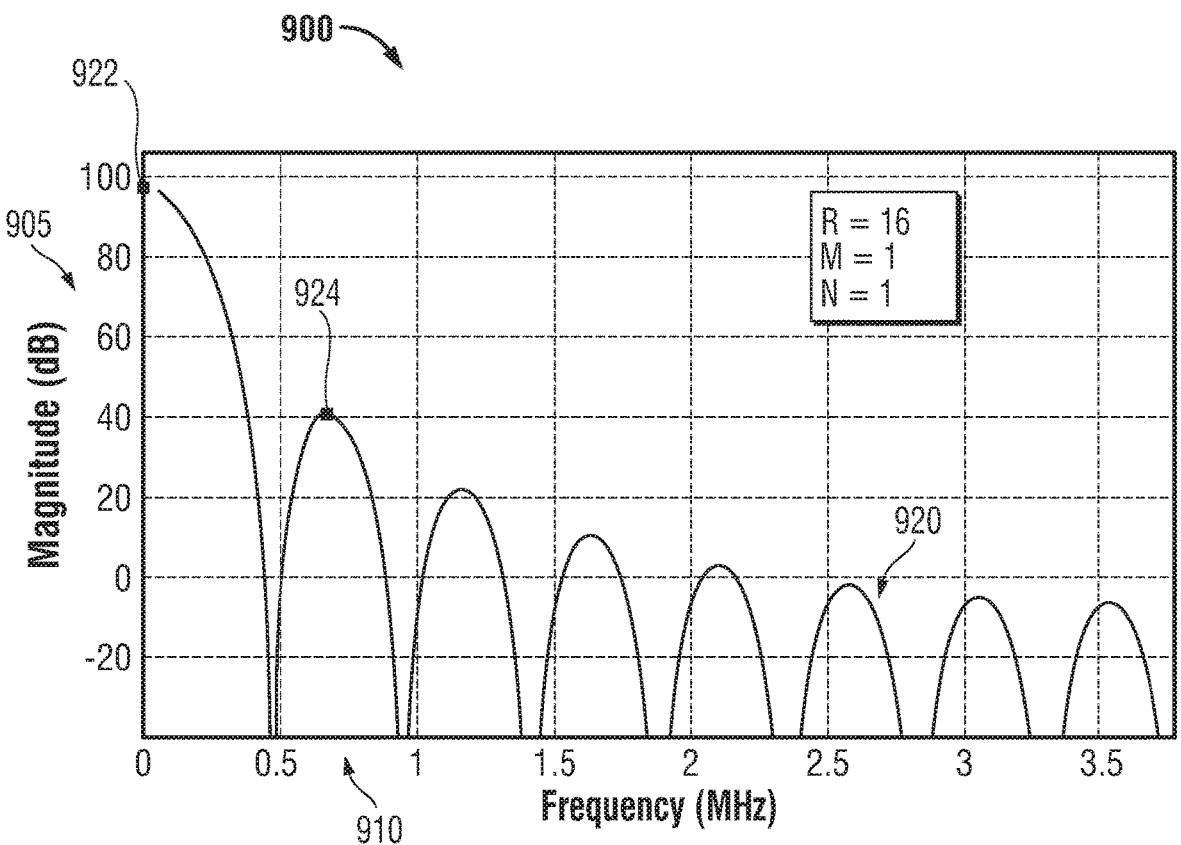
FIGS. 9A and 9B illustrate a frequency domain response and a time domain response, respectively, of the sensed signal in accordance with further embodiments of the Boxcar filter of the present disclosure.
Figure 9B:
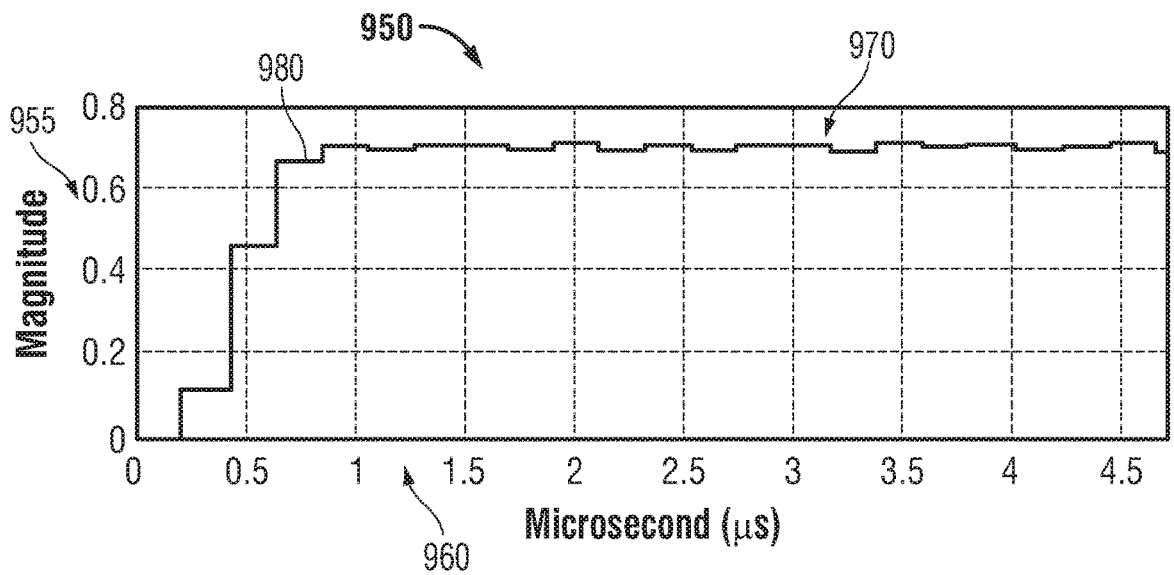

FIGS. 9A and 9B illustrate the frequency response 900 and the signal response 950, respectively, of the Boxcar filter 700 of FIG. 7, which is a fourth-order (i.e., N=4) CIC filter whose decimation factor is 16 (i.e., R=16) and whose differential delay is 1 (i.e., M=1). As shown in FIG. 9A, the first lobe 922 centered at 0 kHz has a magnitude of about 96.30 and the second lobe 924 centered at 667 kHz has a magnitude 43.67. Thus, there is about a −53 dB drop from the first lobe to the second lobe, which is about four times the attenuation provided by the boxcar filter 600 of FIG. 6A.

Referring now to FIG. 9B, the signal response graph 950, which illustrates the signal response 970 corresponding to the frequency response 920 of FIG. 9A, shows a more stable output than the signal response 870 of FIG. 8B after 1.0 µs. The signal response 970, however, shows more group delay than the signal response 870 of FIG. 8B. Specifically, the first-order Boxcar filter 600 has about a 0.2 µs group delay while the fourth-order Boxcar filter 700 has about a 0.8 µs group delay. The signal response 970 oscillates around a magnitude of 0.7. Since the energy at two of the three noise frequencies, namely, 400 kHz and 672 kHz, is sufficiently attenuated due to the −53 dB attenuation provided by the fourth-order boxcar filter 700 of FIG. 7, the oscillations of the signal response are very small.

Figure 10A:
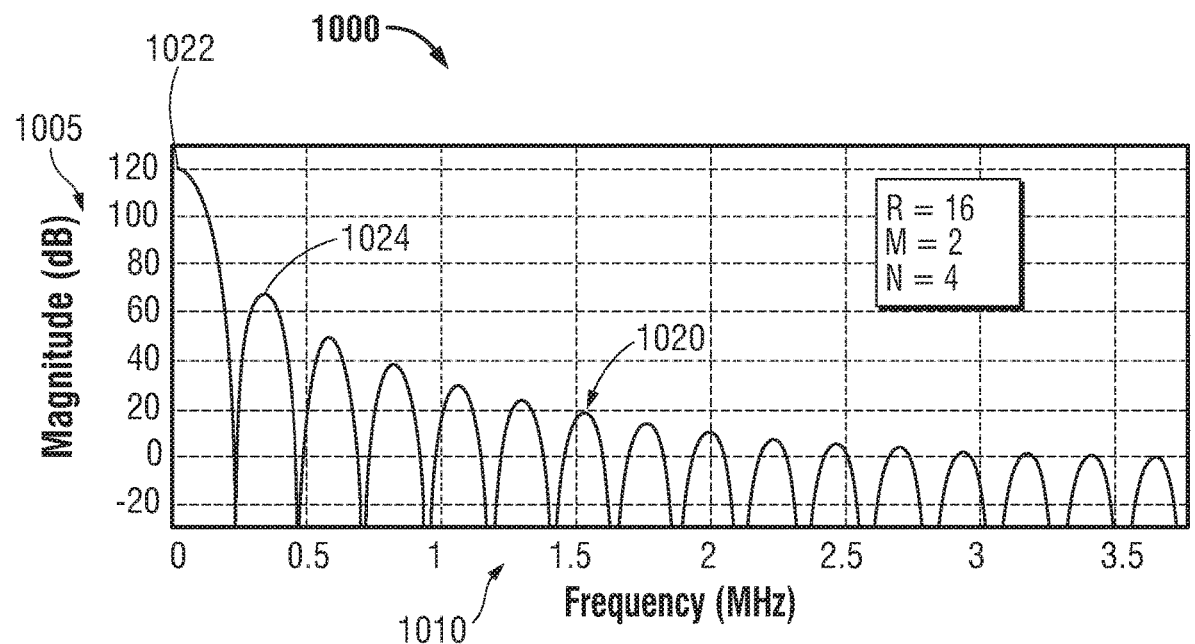
FIGS. 10A and 10B illustrate a frequency domain response and a time domain response, respectively, of the sensed signal in accordance with still further embodiments of the Boxcar filter of the present disclosure.
Figure 10B:
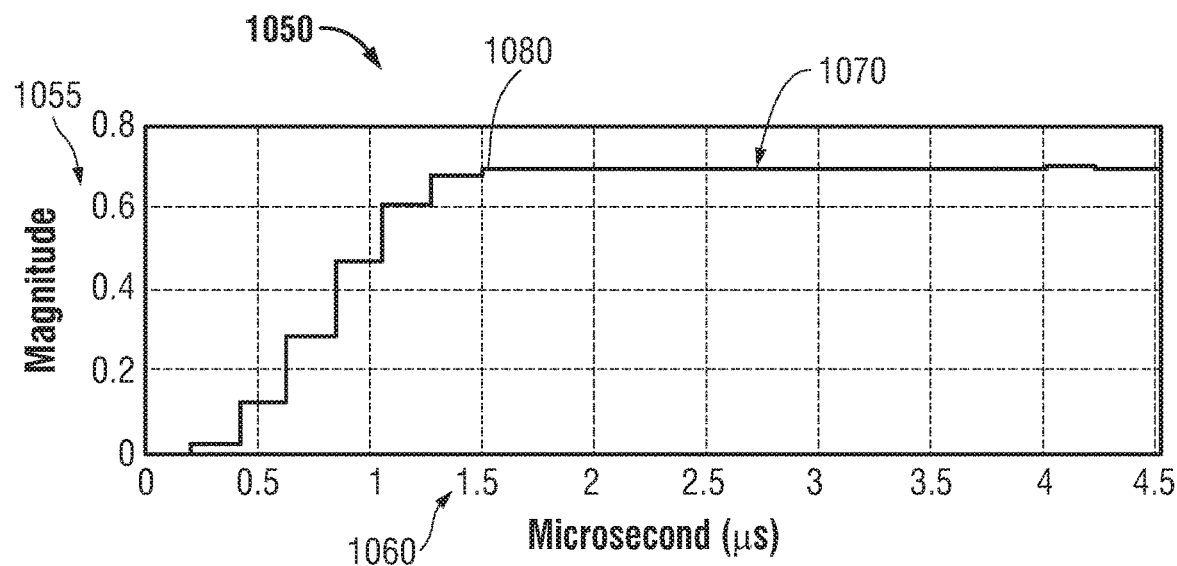

FIGS. 10A and 10B illustrate the frequency response 1000 and signal response 1050 of another embodiment of the Boxcar filter which has a differential delay of two. By increasing the differential delay, the signal response is stabilized. As shown in FIG. 10A, the first lobe 1022 centered at 0 Hz has a magnitude of about 120 dB and the second lobe 1024 centered at 354 kHz has a magnitude of about 67 dB. Thus, there is about a −53 dB drop from the first lobe 1022 to the second lobe 1024. Thus, the change in differential delay does not have any effect on the −53 dB drop. The differential delays, however, double the number of nulls in the frequency response of FIG. 9A. In other words, the nulls are located at multiples of 236 kHz (472 kHz/2), i.e., 236 kHz, 472 kHz, 708 kHz, etc. As described above, the three most influential frequencies of the noise, 200 kHz, 400 kHz, and 672 kHz, are very close to the nulls. Thus, the energy at the three most influential frequencies are more significantly attenuated.

Referring now to FIG. 10B, the signal response graph 1050 shows the most stable output among the three signal responses of the three embodiments of Boxcar filters described in FIGS. 8A-10B. The signal response 1070 shows much more group delay than that in the signal responses in FIGS. 8B and 9B. This group delay is a direct result of the number of filter sections and the value of the differential delay. Since this embodiment has a fourth-order CIC filter and a differential delay of 2, the group delay is 1.5 µs, which is about eight times the group delay of the embodiment in FIGS. 8A and 8B, and is about two times the group delay of the embodiment of FIGS. 9A and 9B. The signal response 1070 is also very stable after the group delay.

Figure 11:
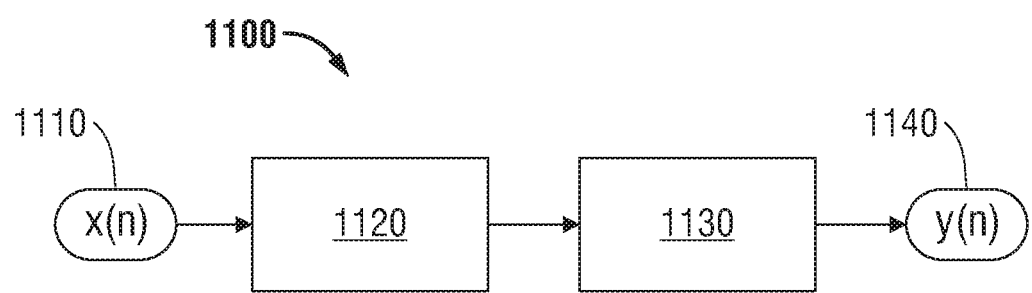
FIG. 11 is a block diagram of an averaging filter in accordance with still further embodiments of the present disclosure.

FIG. 11 is a block diagram of an averaging filter 1100 including a CIC filter 1120, e.g., the first-order CIC filter 600 of FIG. 6A or the fourth-order Boxcar filter 700 of FIG. 7, and a compensation filter 1130 in accordance with other embodiments of the present disclosure. The CIC filter 1120 is a computationally efficient implementation of linear phase finite impulse response (FIR) filters without using multipliers. One of the drawbacks of a CIC filter is that it exhibits passband droop. The compensation filter 1130, however, is applied to the output of the CIC filter 1120 to compensate for the passband droop by narrowing the output bandwidth and flattening the passband gain of the CIC filter 1120. The compensation filter 1130 may have a magnitude response that is the inverse of the CIC filter 1120 and may include a finite impulse response (FIR) filter or an infinite impulse response (IIR) filter. In this way, some noise can be removed efficiently while sacrificing a small group delay.

There are several parameters which can be adjusted in the design of the cascaded filter of FIG. 11:
  The decimation rate and the number of sections of the CIC filter may be adjusted.
  Nulls may be added to the magnitude response if the frequency range of the control signal can be narrowed.
  Different FIR or IIR filter implementations may be selected for the compensator.
  Different cutoff frequencies of the decimating filtering system may be selected.

The cascaded-filter architecture has many benefits. For example, with decimation, the computational complexity of narrowband lowpass filtering can be reduced as compared to a single lowpass FIR filter.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. A method for controlling an electrosurgical generator, comprising:
  generating radio frequency (RF) electrosurgical energy;
  sensing a voltage waveform and a current waveform of the generated electrosurgical energy;
  processing the sensed voltage waveform and the sensed current waveform using a plurality of moving averaging filters, which include first, second, and third moving average filters, to determine a Root Mean Square (RMS) voltage, an RMS current, an average power, and a real part of an impedance; and
  controlling the electrosurgical energy based on at least one of the RMS current, the RMS voltage, the average power, and the real part of the impedance, wherein:
    the first moving average filter outputs a mean square voltage based on the voltage waveform;
    the second moving average filter outputs the average power based on the voltage waveform and the current waveform;
    the third moving average filter outputs a mean square current based on the current waveform; and the real part of the impedance is calculated by dividing the average power by the RMS current.

2. The method according to claim 1, wherein processing the voltage waveform and the current waveform includes:
   squaring, by a first multiplier, the sensed voltage waveform;
   squaring, by a second multiplier, the sensed current waveform;
   multiplying, by a third multiplier, the sensed voltage waveform and the sensed current waveform to obtain a power waveform;
   averaging, by the first moving average filter, the squared voltage waveform to obtain the mean square voltage;
   averaging, by the moving third average filter, the squared current waveform to obtain the mean square current;
   averaging, by the second moving average filter, the power waveform to obtain the average power;
   calculating the RMS voltage based on the average voltage waveform; and
   calculating the RMS current based on the average current waveform.

3. The method according to claim 2, wherein controlling the electrosurgical energy includes:
   generating a control signal based on a difference between the real part of the impedance and a desired real part of the impedance; and
   controlling the generated electrosurgical energy based on the control signal.

4. The method according to claim 1, further comprising sampling the sensed voltage waveform and the sensed current waveform to obtain a predetermined number of samples of each of the sensed voltage waveform and the sensed current waveform.

5. The method according to claim 4, wherein the predetermined number of samples corresponds to an integer multiple of a RF frequency of the voltage waveform and the current waveform.

6. The method according to claim 1, wherein the moving averaging filters are selected from the group consisting of Cascaded Integrator Comb (CIC) filters, boxcar averaging filters, finite impulse response filters, infinite impulse response filters, and any combination of these averaging filters.

7. The method according to claim 1, wherein plurality of moving averaging filters are identical to each other.

8. The method according to claim 1, wherein the plurality of moving averaging filters are low pass filters.

9. The method according to claim 4, further comprising synchronously operating the plurality of moving averaging filters over the same predetermined number of samples of each of the voltage waveform and the current waveform.

10. The method according to claim 1, further comprising calculating phase information between the voltage waveform and the current waveform by dividing the average power by a product of the RMS voltage and the RMS current.

* * * * *